US005465716A

United States Patent [19]
Avitall

[11] Patent Number: 5,465,716
[45] Date of Patent: Nov. 14, 1995

[54] CATHETER CONTROL HANDLE

[76] Inventor: Boaz Avitall, 4868 N. Ardmore Ave., Milwaukee, Wis. 53217

[21] Appl. No.: 156,284

[22] Filed: Nov. 22, 1993

[51] Int. Cl.⁶ .................................................. A61B 17/36
[52] U.S. Cl. ............................. 128/642; 606/41; 607/122
[58] Field of Search ................................... 128/772, 639, 128/642, 656–658; 604/280; 606/46, 129, 41; 607/122, 119, 115

[56]  References Cited

U.S. PATENT DOCUMENTS

| | | |
|---|---|---|
| 3,625,200 | 12/1971 | Muller . |
| 4,033,331 | 7/1977 | Guss et al. . |
| 4,641,654 | 2/1987 | Samson et al. ........................ 604/95 X |
| 4,799,496 | 1/1989 | Hargreaves et al. . |
| 4,846,174 | 7/1989 | Willard et al. ........................ 604/95 X |
| 4,874,371 | 10/1991 | Comben et al. . |
| 4,886,067 | 12/1989 | Palermo ..................................... 128/657 |
| 4,960,134 | 10/1990 | Webster, Jr. . |
| 5,055,109 | 10/1991 | Gould . |
| 5,117,828 | 6/1992 | Metzger et al. . |
| 5,125,896 | 6/1992 | Hojeibane . |
| 5,161,534 | 11/1992 | Berthiaume ............................. 128/657 |
| 5,163,911 | 11/1992 | Sirimanne et al. ................... 128/772 X |
| 5,185,004 | 2/1993 | Lashinski . |
| 5,199,950 | 4/1993 | Schmitt et al. . |
| 5,228,442 | 7/1993 | Imran . |
| 5,238,005 | 8/1993 | Imran . |
| 5,242,441 | 9/1993 | Avitall ................................. 607/122 X |

OTHER PUBLICATIONS

Avitall, Boaz et al, "Physics and Engineering of Transcatheter Cardiac Tissue Ablation", *JACC* vol. 22, No. 3, Sep. 1993:921–32.

*Primary Examiner*—Lee S. Cohen
*Assistant Examiner*—Samuel Gilbert
*Attorney, Agent, or Firm*—Haugen and Nikolai

[57]  ABSTRACT

A catheter control handle for precise spatial placement of a working catheter tip in an organ or vessel of interest is presented that is readily operable with one hand and uses a single operating knob in conjunction with a single control wire connected in the distal working catheter tip area in a manner such that longitudinal translation of the knob produces distal catheter tip deflection and rotation of the knob produces rotation of the deflected tip. The longitudinal translation of the control knob deflects the catheter tip by displacing the proximal portion of the catheter relative to the control wire and the rotation of the control knob applies rotational torque to the control wire.

15 Claims, 3 Drawing Sheets

CATHETER CONTROL HANDLE

BACKGROUND OF THE INVENTION

I. Cross-Reference to Related Application

Reference is made to application Ser. No. 07/989,804, now U.S. Pat. No. 5,327,905 issued Jul. 22, 1994 which is a continuation-in-part of application Ser. No. 07/909,867, now U.S. Pat. No. 5,354,297 issued Oct. 11, 1994 both of common inventorship with the present application. The cross-referenced applications also describe improved catheters and tip orientation or manipulation control systems.

II. Field of the Invention

The present invention is directed generally to an improved catheter navigation or manipulation control system adaptable to any steerable vascular catheter, but particularly for use in the field of cardiac arrhythmia recording and ablation. The invention involves an improved single-knob handle control system that simplifies the control of the highly maneuverable working catheter tip area. The control system allows the operator to hold the control handle and direct the tip of the catheter in multiple directions, i.e., in three-dimensional space, using the same hand to operate the control knob and precisely maneuver the catheter tip. The apparatus is particularly useful in navigating catheter devices with electroded tips in cardiac chambers and around heart valves.

III. Discussion of the Related Art

Certain advantages available with regard to steerable catheter systems have been recognized. Such devices can be inserted into blood vessels or similar bodily areas and their distal end navigated through the tortuous vascular path to reach areas of the body normally inaccessible without surgery. Such navigating catheter devices generally require a certain amount of rigidity, so that the posture of the distal tip can be controlled; but they also need to exhibit a certain amount of flexibility to facilitate intricate navigation of the distal catheter tip. In addition, to facilitate use, steerable catheters ideally should possess the ability both to bend in the plane parallel to the main axis of the catheter and also at the same time to be deflected radially, i.e., in a plane generally perpendicular to that of the main catheter axis so that complete and controlled three-dimensional spatial maneuvering of the tip in, for example, an internal chamber, such as a cardiac chamber, can be realized.

Catheters of the steerable or self-navigating type, having electrode means for monitoring parts of the body, such as for electrically mapping the heart by receiving and transmitting electrical signals related to the operation of that organ to recording signal processing and display devices are also known. The ability to successfully record impulses or signals and from them electrically map the cardiac chambers and valves using flexible catheters having steerable electroded tips has further led to the use of the technique of transcatheter ablation of cardiac tissues that have been identified as the pathways that cause cardiac arrhythmias. This technique has emerged as one of the most important advances in cardiac electrophysiology. Its goal is to destroy the arrhythmogenic tissue without compromising the mechanical or muscular integrity of the cardiac tissues and vessels.

Not long ago, for example, many patients with Wolff-Parkinson-White syndrome or ventricular tachycardia underwent surgical dissection of the arrhythmogenic tissue followed by a painful and prolonged recovery. Introduction of the transcatheter approach has dramatically reduced the suffering and cost of this definitive treatment for many causes of cardiac arrhythmias. The general approach to this procedure initially preferably utilized high energy direct current delivered to the catheter poles, for example, to disrupt the A-V node condition and even to create a complete heart block by ablating the His bundle. More recently, however, radio frequency has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", *JACC*, Volume 22, No. 3:921–32. The rapid clinical acceptance of this procedure and the proliferation of physicians engaged in transcatheter tissue ablation has mandated the development of improved steerable catheter devices.

One earlier steerable catheter device is shown in U.S. Pat. No. 4,785,815 to Webster, Jr. That device includes a catheter tube which carries one or more electrodes at its distal tip for sensing membrane potentials within the heart, together with a heating device for ablating at least a portion of the pathway located by the sensing device. That catheter includes a deflection control which allows the introduction of a curvature to the working tip of the catheter; however, any lateral or radial maneuvering of the deflected or bent tip requires rotation of the entire catheter system. Another catheter device which utilizes a single handle-operated deflection wire to produce curvature in the tip is disclosed in U.S. Pat. No. 4,960,134. A turn-limiting proximal adapter for a steerable catheter system which includes a stationary portion and a rotating portion is shown in U.S. Pat. No. 5,185,004 to Lashinski. That device is utilized to rotate a guidewire, to facilitate the performance of an angioplasty procedure.

Electrophysiological catheter ablation procedures, however, are still hampered by the difficulties encountered by the operator in attempting to maneuver the catheter tip to the precise location of the arrhythmogenic tissue. This is primarily due to the limited maneuverability control afforded by prior catheters. Generally, available catheters, even catheters with single deflection wire control, have been characterized by inadequate control of fine movements and have tips that can be deflected only in planes parallel to the main catheter tube other than by rotating the entire device. This makes the process of aligning electrodes with the precise ablation site of interest a long and tedious affair.

The above cross-referenced applications describe a biplanar deflection system which allows control of the lateral movement of the catheter tip as well as controlling deflection in planes parallel to the main catheter tube. That system employs a controllable element or elements which impart both direct deflection by reciprocation of the control element and lateral deflection by the transmission of rotational torque along the control element. Systems in accordance with those inventions can be assembled utilizing a single control wire or a plurality of control wires. These devices greatly enhance control and facilitate maneuvering of the catheter tip in three-dimensional space, reducing the time required in the addressing of cardiac chamber and valve locations, control of the catheter and maneuvering of the catheter tip generally requires the use of both hands by the operator. There clearly remains a definite need for the development of a full control deflection system that can be operated by a handle control which requires but one hand to hold the catheter and to perform the control functions including fine tuning.

Accordingly, it is a primary object of the present invention to provide an improved control system for improving the controlled navigation of flexible catheter tips.

Another object of the invention is to provide a catheter control handle that can be held and the tip control or navigation system operated all with one hand.

Still another object of the invention is to provide a precise yet mechanically simple system to accomplish complete three-dimensional catheter tip control.

Yet a further object of the invention is to enable complete three-dimensional spatial navigation of a catheter tip utilizing a single control knob.

Other objects and advantages of the invention will occur to those skilled in the art based on a review of the illustrations and descriptions herein.

SUMMARY OF THE INVENTION

By means of the present invention, there is provided a control system for a vascular navigation or steerable catheter in which both the lateral and radial aspects of complete three-dimensional catheter tip control, i.e., the operation of the catheter, can be accomplished using one hand. The invention includes a handle with a single control knob is operated in relation to a control wire or element such that reciprocation and rotation of the knob, respectively, accomplish the desired longitudinal (axial) displacement and rotational torquing of the control element. The handle construction is uncomplicated and achieved at modest cost.

While the control system of the invention is especially beneficial for recording and ablation procedures which involve the precise deployment of one or more electrode devices against the moving inner surface of a heart chamber or valve, and which with current devices may be extremely difficult and time consuming, it will be recognized, however, that such control benefits and is intended to be used with other types of catheters and procedures as well.

In one embodiment, the control handle includes an outer hollow housing member having a closed proximal and an open distal end which describes an hollow internal chamber which contains a plurality of hollow shafts or tubular members. An outer shaft or tubular member slidably mounts in the distal portion of the hollow housing member. The distal end of the outer tubular member is connected to an hollow knob housing member shaped to accommodate a rotatable operating knob which operates the control system, and which, in turn, is connected to the proximal end of a catheter, the navigation of the distal portion of which is sought to be controlled. The hollow interior or chamber of the housing member contains the outer and an inner tubular member both of which are provided with longitudinal internal bores throughout their length. The outer member is seated for reciprocal motion in the distal portion of the hollow chamber of the housing. The inner member is rotatably mounted in fixed longitudinal relation with respect to the hollow chamber of the handle housing at its proximal end and its distal end extends through the inner bore of the outer tubular member and through an aligned bore in the rotatable knob to which it is keyed. The inner tubular member is slidable within the bore of the knob but keyed to rotate with the knob about its longitudinal axis. The rotatable knob housing is fixed longitudinally to the outer shaft or tubular member and the catheter tube such that reciprocation of the knob also produces corresponding reciprocal motion of the outer tubular member with the knob relative to the housing and inner member while rotation of the knob produces rotation of the inner shaft or tubular member. The inner tubular member is provided with a rotation limiting device to limit torque applied to the control member and the outer piston is provided with a reciprocal travel limiting means.

The catheter control element or wire is, at its distal end, anchored or attached to the catheter tip to be controlled and is threaded through the length of the catheter, through the knob and through the inner bore of the inner tubular member and is fixed at its proximal end near the proximal end of the inner tubular member so that it rotates with the inner member. Proximally directed movement of the knob produces corresponding proximal movement of the catheter relative to the control member which causes deflection of the distal catheter tip; conversely, distally directed movement relaxes the tip. In this manner, deflection of the tip of the catheter relative to the anchor location of the distal end of the control wire is produced.

It will be appreciated that the handle can be held and the knob manipulated both reciprocally and rotationally using one hand of the operator. The handle adapts for use with a variety of catheters using control elements of the class described. The system may accommodate electrical conductors or the like as for recording/ablation if desired.

DETAILED DESCRIPTION

The catheter control handle of the invention is designed to enable the skilled practitioner to achieve a greater amount of catheter tip area control while at the same time allowing greater freedom during the procedure by providing a catheter control easily operated using only one hand and yet one which includes both axial displacement (bending) and radial maneuvering (lateral movement) of the catheter tip. Reciprocation or axial displacement of a knob attached to the piston arrangement controls the tension of a deflection control wire attached to the catheter wall distal the desired point of bending and rotation of the same knob produces rotation torque on the wire which produces the desired radial deflection of the tip so that the single-knob combination controls the shape of the tip area and the relative location of the tip in three-dimensional space. While such control is especially beneficial for recording and ablation procedures which involve the precise deployment of one or more electrode devices against the moving inner surface of a heart chamber or valve, and which with current devices may be extremely difficult and time consuming, it will be recognized that such control benefits other types of catheters and procedures as well.

The Figures illustrate the control handle of the invention as used to control a connected catheter device having an electrical aspect, such as would operate a recording and tissue ablation device using a single control element or wire. Such a catheter device is presented in greater detail in the above cross-referenced applications and to the extent necessary, such details are deemed incorporated herein by reference.

Figure 3:
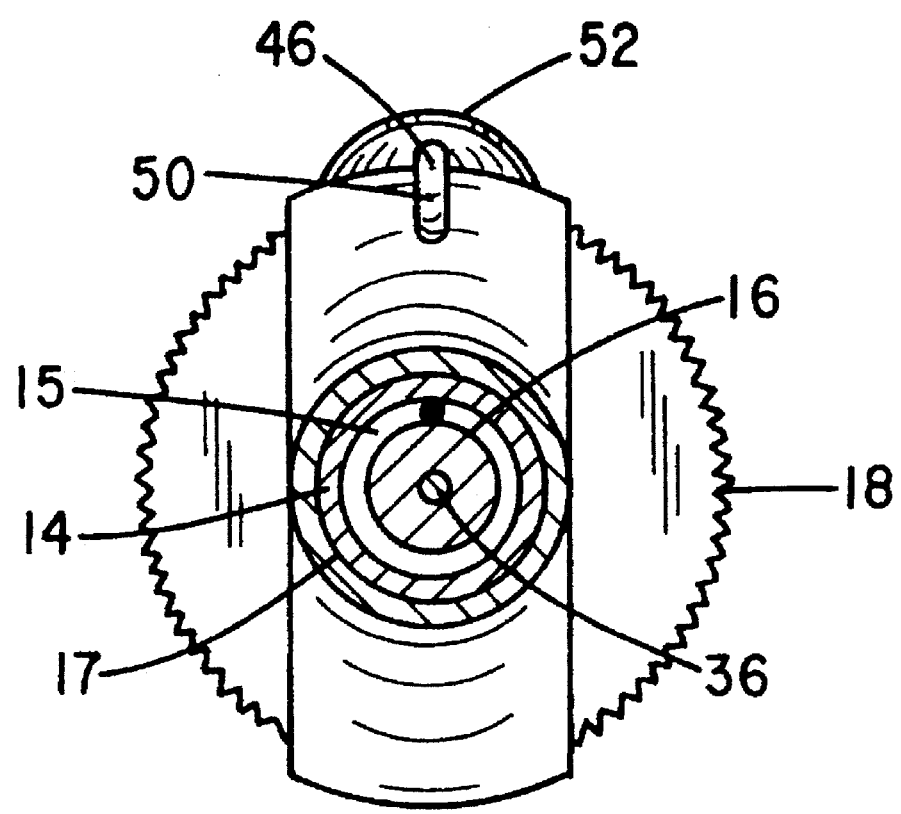
FIG. 3 is a sectional view of certain details of the catheter handle in the vicinity of the handle knob.

The control handle of the invention, generally at 10, includes three main relatively movable cooperating tubular members including a closed ended main or outer hollow handle housing member 12, an upper or outer shaft or tubular member 14 slidably mounted within the distal portion of the member 12 and having a longitudinal inner bore 15 (FIG. 3). A central hollow inner rotatable shaft or tubular member 16 is also mounted in the handle chamber, as detailed below, and extends through the longitudinal bore 15 of the piston 14. The piston member 14 is connected in a fixed manner to the proximal end of a shaped hollow distal connector 17 which is configured to accommodate a knurled knob member 18 exposed in all but two areas on the sides of the member 17. The section or piece 17 further necks down and connects at its distal end to the tube of the catheter to be controlled, represented by proximal fragment 20, as by a lap joint 22.

Figure 1:
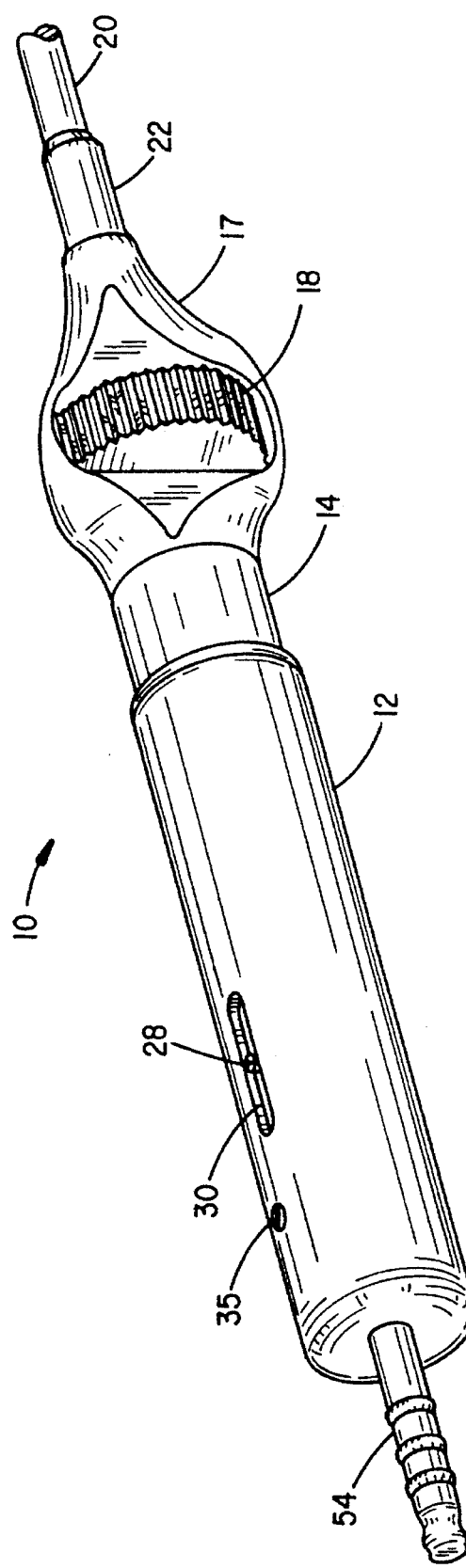
FIG. 1 depicts a perspective view, with parts cut away, of a catheter handle constructed in accordance with the invention.
Figure 2:
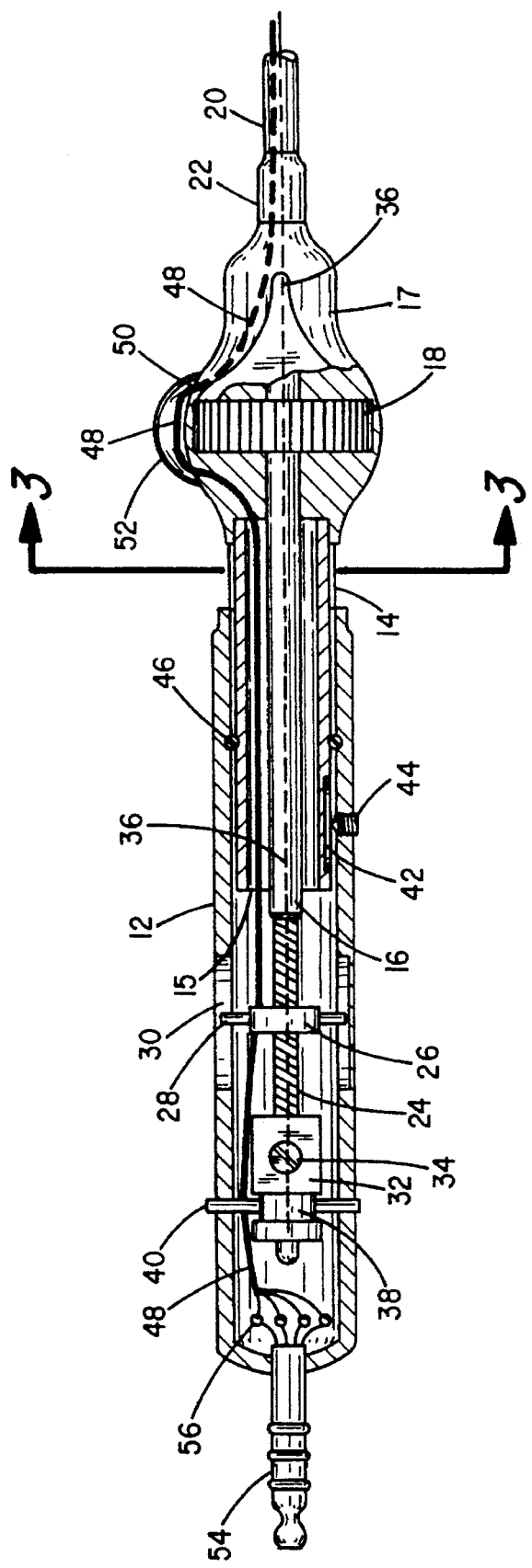
FIG. 2 is an enlarged view, partially in section, of the handle depicted in FIG. 1.

Member 16 has a proximal threaded segment 24 which, in turn, threadably carries a threaded axially displaceable rotation limiting rider member 26. The rider member 26 is provided with one or more extension ears or rotation inhibiting pins 28 which ride along in a longitudinal groove or grooves 30 which may extend through the wall of the member 12 (FIG. 1) so that the member 26 does not rotate with the member 16 but rather is displaced axially along the threaded segment 24 by the rotation of the member 16 within the travel limiting confines of the groove or grooves 30 and, in this manner, limit the rotation of the member 16.

A further hollow control element or proximal wire connection means 32 is fixed to the proximal portion of the member 16 and is provided with a set screw 34 accessible from without the handle as through an opening 35 (FIG. 1) which firmly attaches a control element, represented by the dashed line 36, and which is preferably a deflectable but relatively rigid control wire, to the member 16. The set screw 34 can be used to adjust or set the tension in the control wire. The control wire 36 is threaded through a longitudinal bore in the member 16, hollow member 17 and knob 18 extending distally into a lumen of the catheter 20, where it continues to an anchoring point in the distal section of the catheter sought to be controlled in a well-known manner. The connection means 32 is fixed to and so rotates with the member 16. The member 16 is mounted in the handle with the proximal end thereof fixed in the housing 12 and the distal end extending through, keyed to and slidably supported in a central bore in the knob 18.

Stabilization for guided rotation and longitudinal fixation without reciprocal motion is provided to the member 16 by a mounting that includes recess or groove 38 in the connection means 32, which is centered and allowed to rotate or ride along within a plurality of protruding stabilizing containment or guide members or other fixed restrictive member as at 40. The distal end of the tubular piston member 16 is keyed through the central bore in the knob 18 in a well-known manner so that the rotation of the knob 18 also rotates the member 16 but the keyway further allows the knob 18 to slide reciprocally in relation to and along the member 16.

The hollow tubular member 14 is further provided with a groove 42 which cooperates with a member 44, which may be a set screw, threaded through the outer tubular housing member 12 to predict limits of reciprocal travel of the member 14 relative to the member 12. Axial displacement of the knob 18 produces reciprocation of the piston member 14 within the member 12 which, in turn, produces axial movement of the catheter 20 relative to the fixed control. This relative motion produces deflection of the distal working catheter tip as the control element is displaced relative to the proximal end of the catheter but not the distal end. The control element 36, of course, is free to rotate with member 16 to deliver rotational torque along its length in response to rotation of the knob 18. In this manner, both the application of rotational torque and the bending or deflection of the catheter are readily produced simultaneously by the knob 18.

The knob system is configured so that the knob 18 can rotate freely but may be provided with means to maintain any preset rotational position when released. The rotational knob system is further designed to allow only a predetermined, limited number of rotations, possibly 5 or 6, to each side to prevent the operator from over-torquing the wire which could result in a fracture thereof or other damage. The limits are determined by the length of the slots 30 along the threaded portion 24 of the member 16.

Likewise, the displacement of the shaft 14 within the housing 12 can be provided with friction producing means or the like to maintain any setting, once established. This can consist of one or more O-rings as at 46 which both provide sealing and added friction to the system. Generally, there is sufficient friction between the rotating and reciprocating parts to produce maintainable control.

In the case of a recording/ablation catheter system, the handle system includes provision for the passage of a wire bundle 48 which is threaded through the member 17 and as by using openings as at 50 to safely bypass the knob 18 and through the lumen 15 of the member 14 other mechanisms to connect with a multi-connector plug-in or jack 54 as at proximal connections 56. Of course, the wire bundle 46 is preferably totally enclosed as by a cover 52, which may be integral with the connector 17.

The control element 36 must be flexible but is preferably somewhat stiff or rigid throughout most of its length to allow better control of lateral deflection which requires a highly torqueable wire which is highly flexible only at the end and which is inserted into the flexible deflectable distal portion of the catheter. The proximal portion of this wire may be significantly more rigid. It is threaded through the length of the relatively rigid portion of the catheter and extends into the handle and through to the hand-operated rotatable member 16 through the control knob 18. The distal end of this wire is fixed to the catheter side wall, usually near the tip electrode. Rotation of the knob 18 left or right transmits rotational torque to the catheter tip. When the distal catheter tip is bent or deflected, by the reciprocation of the knob 18, the application of torque through this wire causes the distal tip to deflect laterally.

In operation, the system can readily be manipulated by one hand gripping the handle member 12 and both reciprocally moving the knob 18 and rotating it as desired to maneuver the tip. The invention enables one to control a remote distal catheter tip area in three-dimensional space using a single knob and a single control element. In this manner, bending deflection or bending of the catheter tube is accomplished by longitudinal displacement or reciprocating movement of the knob which displaces the catheter relative to the control wire or member 36. Lateral movement control is achieved by turning or rotating the knob in the desired direction. The combination allows precise positioning of the tip in a heart chamber or other organ yet requires only one of the operator's hands.

It should further be noted that with respect to recording and ablation catheters, the section or sections of flexure in the catheter may be made any length and in any particularly embodied form. The purpose of the control system, of course, is to enable the user to place the one or more ablation and/or recording electrodes in a position to address and hold any specific location in a cardiac chamber or valve surface in the shortest time. Unusual shapes are particularly necessary to address those areas difficult to continually contact using earlier shape control techniques. It will further be understood that any desirable size, spacing and number of recording and/or ablation electrodes can be used. It must be remembered that the catheter must have the ability to place an electrode system in sustained contact with tissue that is essentially constantly in motion, as is the case within a beating heart. The present invention involves control of the catheter and not the specific catheter configuration, however, and so is adaptable to many. Details of exemplary catheters can be found in the above cross-referenced applications and to the extent necessary, such details are hereby deemed incorporated by reference herein.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A catheter system for precise spatial placement of a catheter tip in an organ or vessel of interest by controlling the operation of an associated control element, being operable using one hand, comprising:

(A) a catheter having a working tip including a working tip area;

(B) a control system connected to the catheter for controlling the working tip;

(C) a handle housing means for carrying the control system configured to be gripped and operated with one hand;

wherein said control system comprises (1) single operating knob means for manipulating an associated control element, said operating knob means being connected to said handle housing means and also connected to a proximal end of the catheter to be controlled, said operating knob means further being carried by said handle housing means and mounted for translational and rotational motion relative thereto, said operating knob means including means for allowing the passage of an associated control element therethrough;

(2) control element mounting means for receiving and fixing an associated control element to said handle housing means;

(3) an associated control element having a proximal and a distal end and being fixed at the proximal end to said control element mounting means and being fixed at the distal end to the working tip area of said catheter;

(D) wherein translational movement of said operating knob means produces relative transitional movement between the catheter connected to and moving with said operating knob means and said associated control element thereby deflecting said working tip area of said catheter; and (E) wherein rotational movement of said operating knob means also causes said associated control element to rotate with said operating knob means to radially adjust said working tip area.

2. The apparatus of claim 1 wherein said control element is a control wire.

3. The apparatus of claim 1 further comprising:

(a) a knob housing for carrying said operating knob means;

(b) a first shaft member connected to the knob housing and having a central longitudinal bore;

(c) wherein said operating knob means is mounted in said knob housing which is, in turn, connected between the proximal end of said catheter to be controlled and the first shaft member which is, in turn, slidably carried in a distal portion of said handle housing means;

(d) wherein said operating knob means is provided with a central bore and further comprising a second shaft member mounted to rotate within said handle housing means and the central longitudinal bore of said first shaft member and having a distal end extending through said central bore in said operating knob means, the distal end being keyed to rotate with but free to slide longitudinally with respect to said operating knob means; and (e) wherein the proximal end of said control element is fixed to said second shaft member to thereby rotate with the rotation of said operating knob means.

4. The apparatus of claim 3 wherein said second shaft member extends coaxially through the central longitudinal bore in said first shaft member and has a proximal end, the proximal end being rotatably mounted in fixed longitudinal relation in the handle housing means proximal said first shaft member, said second shaft member having a central bore for containing said control element, the proximal end of which is adjustably fixed to said second shaft.

5. The apparatus of claim 4 further comprising means for limiting rotation of said operating knob means comprising a threaded proximal section, in said second shaft member, a non-rotating rider member threadably carried thereon and longitudinally displaced by the rotation of said second shaft means and means associated with said rider member for limiting translational displacement thereof.

6. The apparatus of claim 3 further comprising means for limiting translational travel of said operating knob means further comprising a groove having a length, in an outer wall of said first shaft member and cooperating stop means inwardly projecting from said housing means into said groove for limiting the translational travel to the length of said groove.

7. The apparatus of claim 3 further comprising electrical connector means for connecting electrical conductors on said handle housing means and passage means in said knob housing for allowing passage of a plurality of electrical conductors from said catheter through the handle housing to connect to said electrical connector housing.

8. The apparatus of claim 1 including means for fixing said operating knob means in a desired position.

9. The apparatus of claim 8 including means for limiting translational travel of said operating knob means comprising at least one sealing O-ring between the handle housing means and said first shaft member.

10. The apparatus of claim 1 further comprising means for limiting translational travel of said operating knob means.

11. The apparatus of claim 1 further comprising means for limiting rotation of said operating knob means.

12. The apparatus of claim 1 further comprising means for limiting both translational travel and rotation of said operating knob means.

13. A steerable vascular catheter comprising:
(a) a steerable elongated tubular vascular catheter having a proximal and a distal end;
(b) a control handle means for attachment to the proximal end of said catheter, navigation of a distal portion of which is sought to be controlled, said handle means comprising:
  (1) an outer housing means for adjusting a control element, having a closed proximal end and an open distal end and describing a hollow chamber, said distal end being adapted to receive reciprocally a first tubular member,
  (2) first tubular member having proximal and distal ends and a longitudinal bore therethrough mounted in and movable reciprocally within said outer housing means, the distal end connected to the proximal end of said steerable vascular catheter so that said steerable vascular catheter moves with the first tubular member,
  (3) second tubular member having proximal and distal ends and a longitudinal bore therethrough rotatably mounted in said outer housing means,
  (4) single operating knob means having a central bore therethrough connected to operate said first tubular member reciprocally within said outer housing means and rotate said second tubular member relative to said outer housing and said first tubular member wherein the distal end of the second tubular member is carried in the central bore,
(c) control element having a proximal and a distal end for navigating the distal end of said steerable vascular catheter, said control element having a proximal end fixed to said second tubular member and a distal end fixed at a location in the distal end of said steerable catheter sought to be controlled such that reciprocal displacement and rotation of said single operating knob means control the spatial disposition of said distal end of said catheter sought to be controlled.

14. The apparatus of claim 12 further comprising knob housing means for carrying said operating knob means connected between said first shaft member and the proximal end of said catheter, said single operating knob means being freely rotatable within said knob housing means.

15. The apparatus of claim 12 further comprising electrical connector means for connecting electrical conductors on said proximal end of said outer housing means and means for allowing passage of a plurality of electrical conductors through said control handle means to connect to said electrical connector means.

* * * * *

UNITED STATES PATENT AND TRADEMARK OFFICE
CERTIFICATE OF CORRECTION

PATENT NO. : 5,465,716

DATED : November 14, 1995

INVENTOR(S) : Boaz Avitall

It is certified that error appears in the above-identified patent and that said Letters Patent is hereby corrected as shown below:

In column 8, claim 2, line 2 please insert --associated-- after the word "said".

In column 8, claim 7, line 53 please insert --means-- after the word "housing".

Signed and Sealed this

Thirtieth Day of July, 1996

Attest:

BRUCE LEHMAN

*Attesting Officer*  *Commissioner of Patents and Trademarks*